(12) United States Patent
Blair, III

(10) Patent No.: US 8,721,569 B2
(45) Date of Patent: May 13, 2014

(54) PHYSICAL THERAPY DEVICE

(76) Inventor: Gordon Talmadge Blair, III, Denver, CO (US)

(*) Notice: Subject to any disclaimer, the term of this patent is extended or adjusted under 35 U.S.C. 154(b) by 217 days.

(21) Appl. No.: 13/402,785

(22) Filed: Feb. 22, 2012

(65) Prior Publication Data

US 2013/0218052 A1 Aug. 22, 2013

(51) Int. Cl.
*A61B 5/00* (2006.01)
(52) U.S. Cl.
USPC ........................................... 600/595
(58) Field of Classification Search
USPC .......... 600/587, 592, 595; 601/23, 27, 33, 34, 601/35
See application file for complete search history.

(56) References Cited

U.S. PATENT DOCUMENTS

| | | | |
|---|---|---|---|
| 5,284,345 A | | 2/1994 | Jehn |
| 5,575,294 A | * | 11/1996 | Perry et al. ..................... 600/587 |
| 5,752,633 A | * | 5/1998 | Antaki .......................... 224/222 |
| 5,879,239 A | | 3/1999 | Macroglou |
| 6,234,982 B1 | * | 5/2001 | Aruin ............................. 600/595 |
| 6,902,493 B1 | | 6/2005 | Rhodes et al. |
| 7,582,064 B2 | * | 9/2009 | Martindale et al. ........... 600/592 |
| 7,803,059 B2 | | 9/2010 | Zhang |
| 8,373,657 B2 | * | 2/2013 | Hildreth ....................... 345/158 |
| 2006/0040757 A1 | | 2/2006 | Rosselli |
| 2011/0074680 A1 | | 3/2011 | Moore |

* cited by examiner

*Primary Examiner* — Max Hindenburg
(74) *Attorney, Agent, or Firm* — Mark D. Trenner; Trenner Law Firm, LLC

(57) ABSTRACT

A physical therapy device is disclosed. An example of the physical therapy device includes a cuff for attachment to a patient's limb. The example physical therapy device also includes a light emitter mounted to the cuff. The example physical therapy device also includes a tracking pattern corresponding to at least one physical therapy exercise. The patient performs the physical therapy exercise by moving the patient's limb in such a manner so as to track light from the light emitter on the tracking pattern.

20 Claims, 5 Drawing Sheets

PHYSICAL THERAPY DEVICE

BACKGROUND

Following an injury (e.g., sports related or due to an automobile accident), the injured person often has to perform physical therapy to regain functional control of their lower extremities. One goal of physical therapy may be achieving proper biomechanics during normal everyday functional movements. Faulty biomechanics in the lower extremity, due to various muscular impairments, has in the past been linked to injury and poor prognosis. Various verbal and tactile cues are made in attempt to correct faulty biomechanical movement of a person's limbs during functional movement. In addition to postural cues, general strengthening of muscles thought to aid in desired motion, or control faulty movement pattern, is also included. If a person does not gain proper control of their functional movements, the person may suffer setbacks or be at increased risk of injury during functional activity. After some time, the insurance may stop paying for the physical therapist and/or the patient wants to continue therapy in the convenience of his or her own home. If the patient is unable to properly perform the therapy without the assistance of a trained physical therapist, the patient may suffer setbacks.

DETAILED DESCRIPTION

Physical therapy is often facilitated by a trained physical therapist. It is desired to use all methods available to give the patient optimal feedback during their functional movements, as to make the person aware if there are performing movements with faulty biomechanics. A physical therapy device is disclosed herein which facilitates neuromuscular control and neuromuscular rehabilitation. Concerning post injury, persons with poor muscular control, or in patient with post-operative condition, the patient often needs to re-gain functional control of their lower extremity. Research has shown the majority of ACL tears and injuries occur in an action including combined motion of internal rotation at the hip on a planted foot, and valgus moment at the knee. Research has also shown that patients with poor neuromuscular control, weak gluteus medius muscles, and weak quadriceps acting in eccentric contraction, demonstrate excessive internal rotation at the hip and an inward valgus moment at the knee during a single leg squat. Physical therapists train these patients to perform actions such as a single leg squat, or landing from a jump, with proper knee control.

Faulty hip and knee mechanics can be judged by a physical therapist by watching the amount of valgus occurring at the knee during such motion. Methods of correcting have conventionally been verbal cues such as "keep your knee in line with your big toe" and/or having the patient watch their knee in a mirror to focus on the direction in which the knee is pointing during knee flexion maneuvers.

The physical therapy device disclosed herein gives patients a visual guided exercise, with visual feedback of where their knee is in space, to allow a better guide for motion. The device may be used by therapists, patients, or both, and enhances the patient's experience during physical therapy at a clinic and/or enables the patient to continue therapy in the convenience of his or her own home without the assistance of a trained physical therapist.

An example physical therapy device includes a light-guide mounted to a limb of the patient. The physical therapy device may be used in conjunction with a training device, wherein the patient may train the light to follow predetermined pattern(s) to properly perform physical therapy exercise(s).

Before continuing, it is noted that as used herein, the terms "includes" and "including" mean, but is not limited to, "includes" or "including" and "includes at least" or "including at least." The term "based on" means "based on" and "based at least in part on."

Figure 1A:
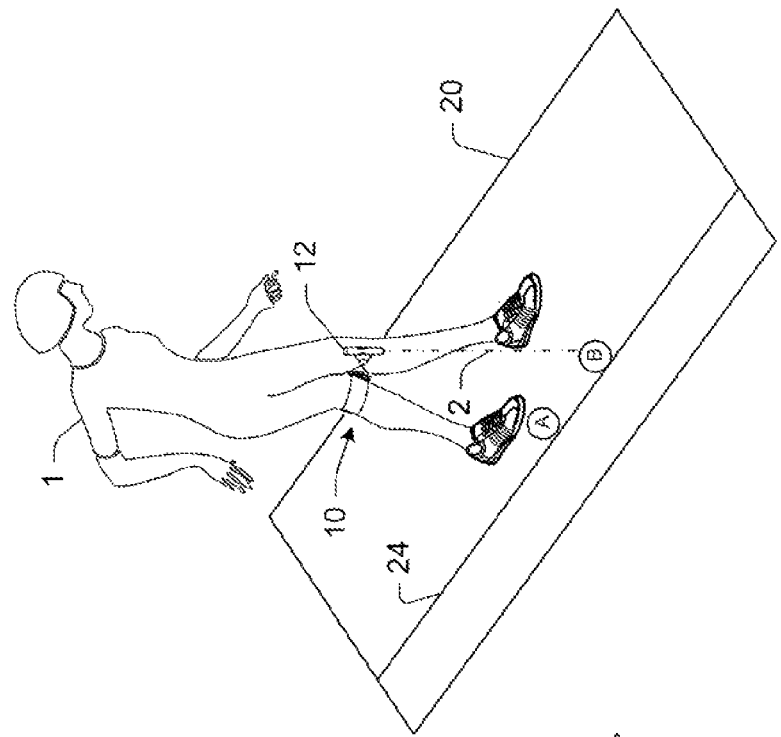
FIGS. 1a-b illustrates use of an example physical therapy device by a patient with a tracking pattern.
Figure 1B:
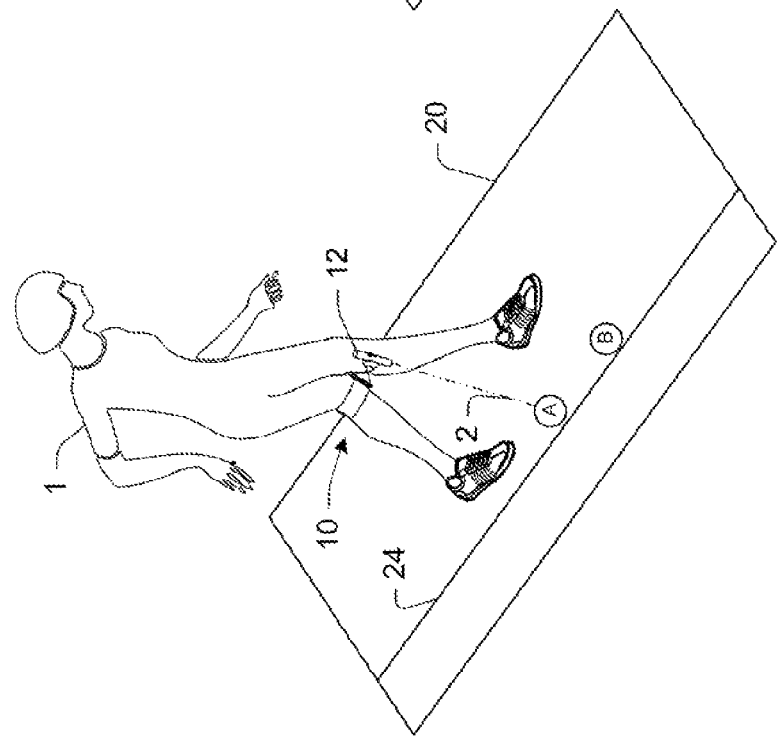

FIGS. 1a-b illustrates use of an example physical therapy device 10 by a patient 1 with a tracking pattern. The physical therapy device 10 may be implemented as a visually guided device including a laser mount shown in FIGS. 1a-b attached, for example to a patient's knee. The physical therapy device 10 may also be attached to the patient's thigh, ankle, calf, or other part of the patient's leg. The device may also be attached to the patient's arm, shoulder, or elsewhere such as around the patient's waist or chest. In another example, the device may even be attached around the patient's wrist or finger(s).

The physical therapy device 10 may include a light emitter 12, such as but not limited to a laser or light-emitting diode (LED) assembly. During use, light 2 is projected onto a tracking pattern 20 to assist the patient 1 perform a physical therapy exercise, such as but not limited to a knee bend as illustrated in FIGS. 1a-b. Movement of the light 2 can be tracked using the tracking pattern 20 (e.g., between points A and B along a straight line as the patient is flexing his or her knee). The patient 1 and/or an aide, such as a physical therapist or other assistant to the patient, can readily determine if the patient 1 is maintaining proper motion throughout the physical therapy exercise (e.g., movement in a straight plane), or if the patient's movement is deviating from a desired pattern of movement. The light 2 may also serve as a visual marker for internal rotation or knee valgus, and allows the patient 1 to correct this motion.

Figure 2A:
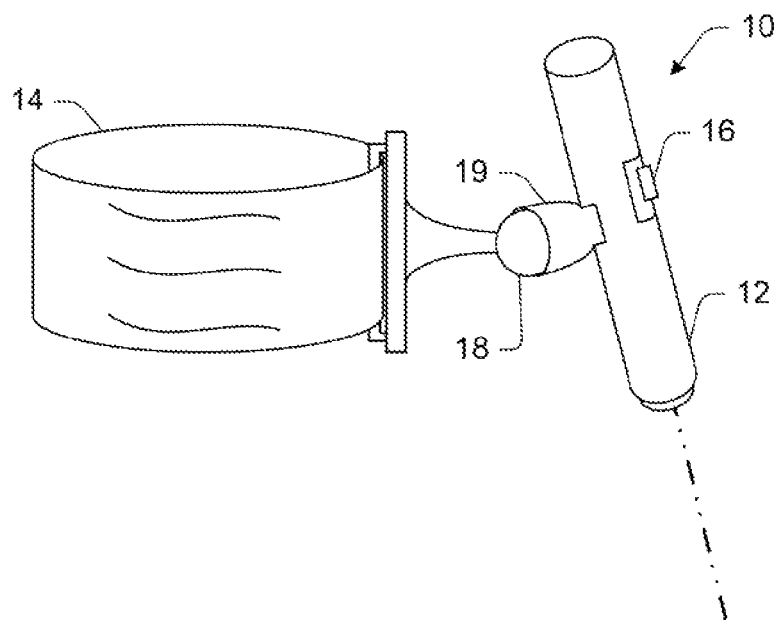
FIGS. 2a-b are detailed views of the physical therapy device shown in different example configurations.
Figure 2B:
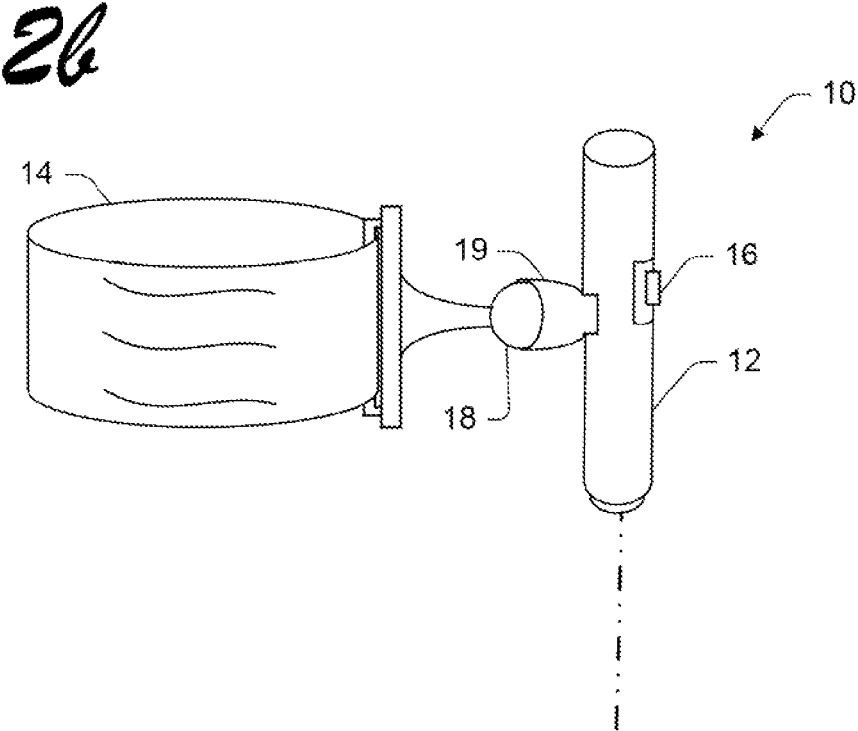

FIGS. 2a-b are detailed views of the physical therapy device 10 shown in different example configurations. In FIG. 2a, the physical therapy device 10 is shown with the light emitter 12 in an angled or somewhat forward facing configuration. In FIG. 2b, the physical therapy device 10 is shown with the light emitter 12 in a substantially perpendicular configuration (relative to the floor).

The physical therapy device 10 includes a cuff 14 for attachment to a patient's limb. The cuff 14 may be made of elastic, or other material such as a strap and buckle. In any configuration, the cuff 14 may make a solid connection with the patient so as not to slide or rotate unnecessarily relative to the patient's limb.

Light emitter 12 may be battery operated and is shown having an on/off switch 16. The light emitter 12 is mounted to the cuff 14. In an example, the light emitter 12 is mounted to the cuff 14 to be fixed in a predetermined position, and the only motion depicted by the light is thus the result of the patient moving his or her leg or other body part, and not a result of the light emitting device 12 moving relative to the cuff 14. That is, the light emitter 12 is fixed or stationary relative to the cuff 14.

But in an example, the light emitter 12 may be purposefully moved. That is, the light emitter 12 may be attached to the cuff 14 using a ball 18 and socket 19 connection as shown in FIGS. 2a-b. The ball 18 and socket 19 connection may provide a stiff or rigid connection so that the light emitter 12 does not move relative to the cuff 14 unless purposefully moved for repositioning by the user.

It is noted that during the exercise, the light emitter 12 is not moving on the mount. The light emitter 12 may need to be moved to start, to align the projected light output (e.g., dot or arrow showing on the desired gridline on the tracking pattern 20). But from then on, it is a dynamic movement of the emitted light by motion of the patient; the light emitter 12 position on the cuff remains unchanged. When the patient steps their right foot onto the foot box, the laser is strapped to the right knee, and then fine adjustments may be made to place the projected arrow in the center of the line 24a-c (see FIG. 3), for example using the ball-in-socket design. After it is relatively aligned with the gridline, the patient actively does a squat, or single leg squat or other physical therapy exercise while keeping the light projection in the bounds of the gridline.

The light emitter 12 and cuff 14 shown in FIGS. 2a-b is only illustrative and not intended to be limiting. Those having ordinary skill in the art will envision other means for attaching the light emitter to the cuff, and the cuff to the patient, after becoming familiar with the teachings herein.

Figure 3:
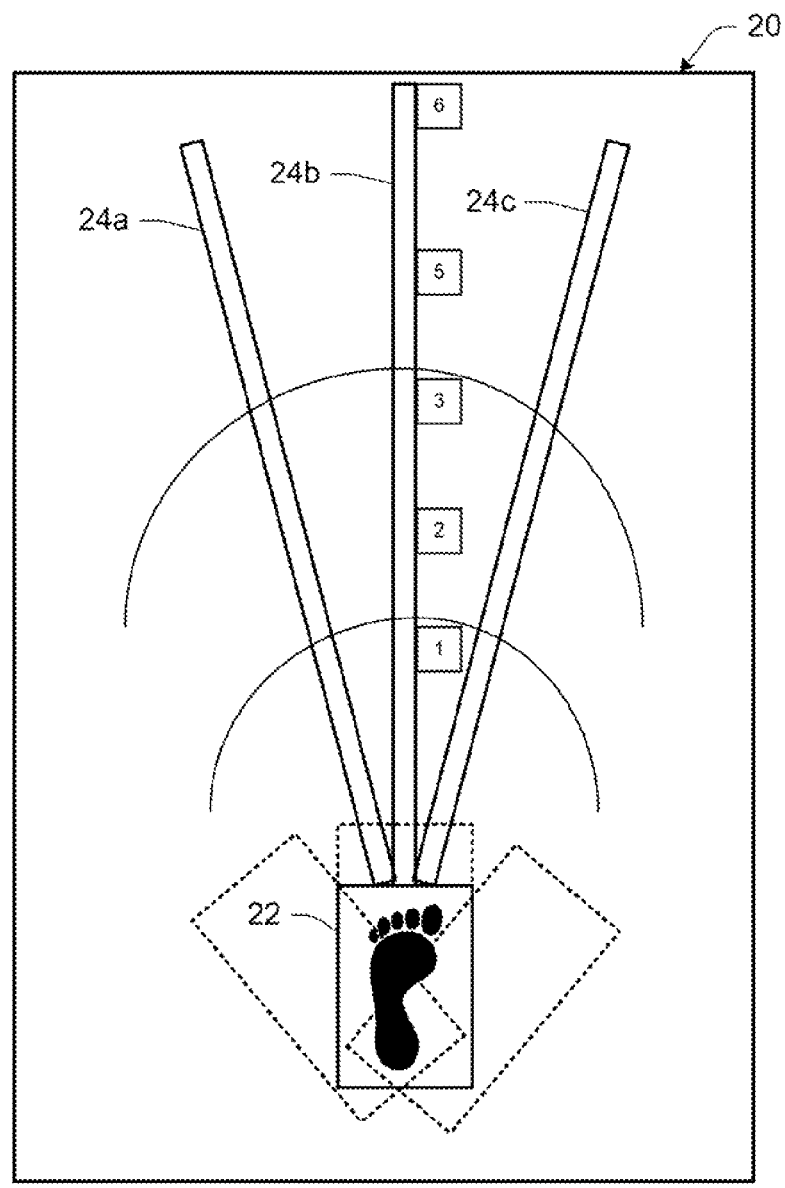
FIG. 3 is a detailed view of an example tracking pattern.

The physical therapy device 10 may be used in conjunction with a tracking pattern 20. FIG. 3 is a detailed view of an example tracking pattern 20. The tracking pattern 20 may correspond to at least one physical therapy exercise. In an example, the tracking pattern 20 is depicted (e.g., by printing or painting) on a mat that can readily be transported and set up in any suitable location at the patient's convenience. The patient performs the physical therapy exercise by moving his or her limb in such a manner so as to track light from the light emitter on the tracking pattern (e.g., as illustrated in FIGS. 1a-b).

In an example, the tracking pattern 20 includes a foot box 22 in the tracking pattern 20 to assist the patient in properly position his or her foot in the tracking pattern 20. The foot box may be any suitable surface type, such as but not limited to semi-rigid foam to soft foam. The foot box serves as a guide to where the patient can place their foot which they are to use during functional movements with visual guidance.

The foot box 22 may be configurable based on the patient (e.g., foot size and/or shape, as illustrated for different sizes in outline in FIG. 3). The foot box 22 may be configurable based on the physical therapy exercise (e.g., rotatable into different starting positions corresponding to different types of physical therapy exercises, as illustrated in outline in FIG. 3).

The foot box 22 may be on the same side as the limb with the mounted light emitter 12. Track 24b is projecting off the foot box at mid point. A patient post right ACL surgery would be standing with their right foot in the "foot box 22 and projecting an arrow down a line with their right knee.

The tracking pattern 20 may include any pattern or patterns. For example, the pattern may be provided as a single strip of reflective tape which the patient uses to track the light. The light may be projected in the shape of an arrow, for example, by providing shading in the shape of an arrow at the light emitting tip of the light emitter 12. The patient tracks the projection of the light in the shape of an arrow along the tape. Other projection shapes may also be provided.

It is noted that the tracking pattern 20 may correspond to more than one physical therapy exercise. For example, the tracking pattern 20 may be pre-printed with multiple physical therapy exercises in a one-size-fits-all approach (e.g., several exercises and levels are illustrated in FIG. 3). In another example, the tracking pattern may be pre-printed only with certain types of physical therapy exercises (e.g., all exercises a patient having a particular type of injury would need). In another example, each tracking pattern may be specific to a particular physical therapy exercise, and the patient (or physical therapist) changes out the tracking pattern based on the exercise being performed.

The physical therapy device 10 and tracking pattern 20 may further include a patient feedback loop. In an example, the tracking pattern 20 may include a coating that responds differently to light. By way of illustration, a highly reflective coating may be provided along a track (e.g., tracks 24a-c shown in FIG. 3) the patient should be following to properly execute the physical therapy exercise, so that the patient (or other user) can easily see the light. A highly light absorbing coating may be provided over areas the user should not be directing light onto (e.g., outside of the tracks 24a-c in FIG. 3), so that the patient cannot see the light as well or at all in these areas. Thus when the patient no longer sees light being reflected back brightly in the tracks 24a-c, this serves as a visual reminder that the patient is not properly performing the exercise.

Other coatings may also be used with different reflective properties, such that the light is reflected as one color when the user is properly performing the physical therapy exercise, and as a different color when the user is improperly performing the physical therapy exercise. That is, the light emitter 12 appears to be emitting a first color light when light from the light emitter 12 is directed by the patient onto the tracking patterns 24a-c, and the light emitter 12 appears to be emitting a second color light when light from the light emitter 12 is directed by the patient outside the tracking patterns 24a-c.

Figure 4:
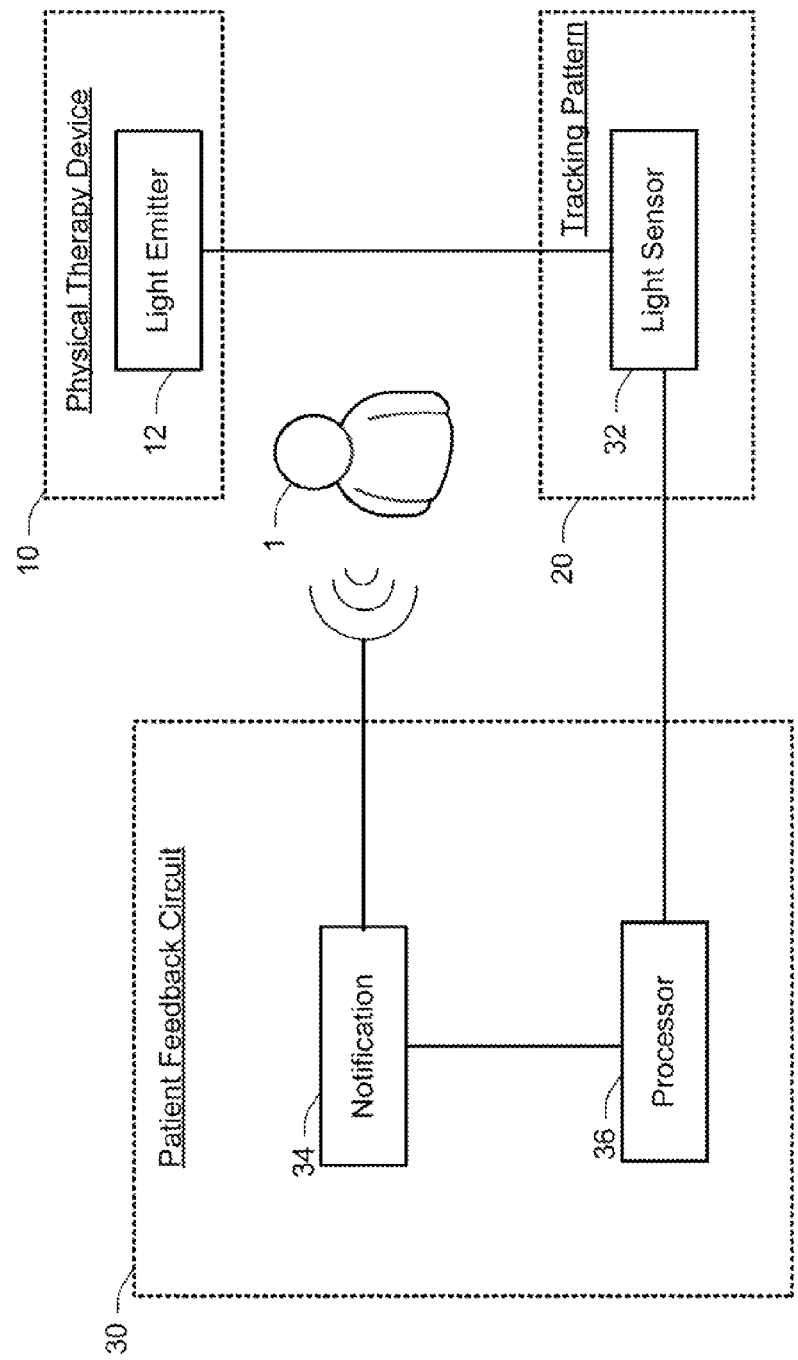
FIG. 4 is a block diagram of an example electronic circuit which may be used to automatically guide the patient to use the physical therapy device in performing a physical therapy exercise.

More sophisticated patient feedback loops may also be provided to automatically notify the patient of proper and improper performance of the physical therapy exercise. FIG. 4 is a block diagram of an example electronic circuit 30 which may be used to automatically guide the patient to use the physical therapy device 10 in performing a physical therapy exercise. It is noted that the functional blocks may be readily implemented in circuitry and program code (e.g., firmware) by one having ordinary skill in the art after becoming familiar with the teachings herein.

The patient feedback loop 30 may include an electronic light receiver 32 in the tracking pattern 20 to detect presence of light. Any suitable light sensor may be used as the light receiver 32 to detect the presence of light. The light sensor(s) may be embedded at one or more position in the tracking pattern 20 (e.g., in the tracks 24a-c in FIG. 3).

The light sensor 32 may be connected (wired or wirelessly) to an electronic patient notification device 34 to notify the patient 1 of various parameters. For example, a processor 36 or other control logic may be provided to receive input from the light sensor(s) 32 and issue a notification if the light receiver 32 detects light in the tracking pattern (e.g., tracks 24a-c in FIG. 3), thus indicating that the patient 1 is properly performing the physical therapy exercise. The electronic patient notification device may notify the patient 1 if the light receiver 32 does not detect light in the tracking pattern, thus indicating that the patient 1 is improperly performing the physical therapy exercise and corrective action is needed.

More sophisticated feedback may also be provided. For example, the electronic patient notification device may notify the patient if the light receiver does not detect light moving in the tracking pattern 20 at a predetermined speed. The electronic patient notification device may notify the patient if the light receiver does not detect light moving in the tracking pattern 20 at a predetermined direction. The electronic patient notification device may notify the patient if the light receiver does not detect light moving in the tracking pattern 20 to a predetermined level (e.g., levels 1-6 shown in FIG. 3).

The notification may be made by any suitable output device 34, and may be an audible warning (a buzzer or bell, or even a recorded voice), a visual warning (e.g., a green/yellow/red light, wherein green indicates proper performance, yellow is cautionary, and red indicates improper performance), or a combination of these or other notifications.

Before continuing, it should be noted that the examples described above are provided for purposes of illustration, and are not intended to be limiting. Other devices and/or device configurations may be utilized to carry out the operations described herein.

Figure 5:
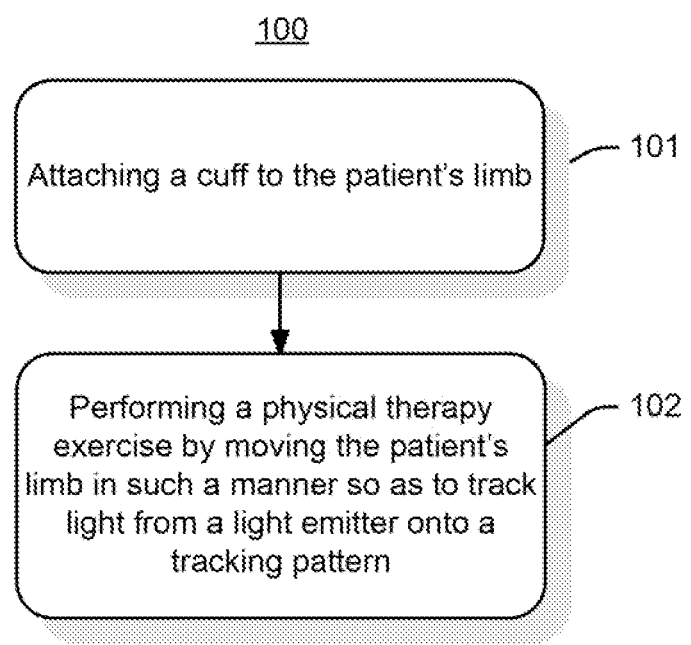
FIG. 5 is a flow chart showing example use of the physical therapy device in performing a physical therapy exercise.

FIG. 5 is a flow diagram 100 showing example use of the physical therapy device in performing a physical therapy exercise. An example method of using the physical therapy device includes at 101 attaching a cuff to the patient's limb, wherein a light emitter is mounted to the cuff; and at 102 performing a physical therapy exercise by moving the patient's limb in such a manner so as to track light from the light emitter onto a tracking pattern.

The method may further include positioning the patient's foot in a predetermined position relative to the tracking pattern. The method may further include automatically notifying the patient of proper and improper use of the tracking pattern.

The operations shown and described herein are provided to illustrate example implementations. It is noted that the operations are not limited to these steps and/or the ordering shown. Still other operations and ordering of the operations may also be implemented.

It is noted that the examples shown and described are provided for purposes of illustration and are not intended to be limiting. Still other examples are also contemplated.

The invention claimed is:

1. A physical therapy device, comprising:
a cuff for attachment to a patient's limb;
a light emitter mounted to the cuff; and
a tracking pattern corresponding to at least one physical therapy exercise, wherein the patient performs the physical therapy exercise by moving the patient's limb in such a manner so as to track light from the light emitter on the tracking pattern, wherein the light tracked on the tracking pattern indicates to a user when the patient's limb is moving in a desired pattern of movement and when the patient's limb is deviating from the desired pattern of movement.

2. The physical therapy device of claim 1, further comprising a foot box in the tracking pattern to properly position the patient's foot in the tracking pattern for a particular physical therapy exercise.

3. The physical therapy device of claim 1, wherein the foot box is configurable based on the physical therapy exercise.

4. The physical therapy device of claim 1, wherein the tracking pattern includes different physical therapy exercises.

5. The physical therapy device of claim 1, further comprising a patient feedback loop and wherein the light emitter emits a first color light when light from the light emitter is in the tracking pattern.

6. The physical therapy device of claim 1, further comprising a patient feedback loop and wherein the light emitter appears to emit a second color light when light from the light emitter is outside the tracking pattern.

7. The physical therapy device of claim 1, further comprising a patient feedback loop and wherein the patient feedback loop includes an electronic light receiver in the tracking pattern to detect presence of light.

8. The physical therapy device of claim 7, further comprising an electronic patient notification device to notify the patient if the light receiver detects light in the tracking pattern.

9. The physical therapy device of claim 7, further comprising an electronic patient notification device to notify the patient if the light receiver does not detect light in the tracking pattern.

10. The physical therapy device of claim 7, further comprising an electronic patient notification device to notify the patient if the light receiver does not detect light moving in the tracking pattern at a predetermined speed.

11. The physical therapy device of claim 7, further comprising an electronic patient notification device to notify the patient if the light receiver does not detect light moving in the tracking pattern at a predetermined direction.

12. A method of using a physical therapy device, comprising:
attaching a cuff to the patient's limb, wherein a light emitter is mounted to the cuff; and
performing a physical therapy exercise by moving the patient's limb in such a manner so as to track light from the light emitter onto a tracking pattern, wherein the light is tracked on the tracking pattern including a gridline boundary, the gridline boundary indicating to a user when the patient's limb is moving in a desired pattern of movement and when the patient's limb is deviating from the desired pattern of movement.

13. The method of claim 12, further comprising positioning the patient's foot in a predetermined position relative to the tracking pattern.

14. The method of claim 12, automatically notifying the patient of proper and improper use of the tracking pattern.

15. A system for physical therapy, comprising:
means for attaching a light emitter to a patient; and
means for guiding the patient to perform a physical therapy exercise by tracking light from the light emitter onto a tracking pattern, the means for guiding including a gridline, and wherein a combination of the tracked light within a boundary of the gridline indicates the patient's limb is moving in a desired pattern of movement and the combination of the tracked 1i ht outside of the boundary of the gridline indicates the s atient's limb is deviating from the desired pattern of movement.

16. The system of claim 15, further comprising means for positioning the patient in a predetermined position relative to the tracking pattern.

17. The system of claim 15, further comprising means for automatically notifying the patient of proper and improper use of the tracking pattern.

18. The physical therapy device of claim 1, wherein a plurality of different physical therapy exercises are pre-printed on the tracking pattern.

19. The physical therapy device of claim 1, wherein a plurality of different exercises corresponding to a particular type of physical therapy are pre-printed on the tracking pattern.

20. The physical therapy device of claim 1, wherein the tracking pattern includes a coating that responds differently to light.

* * * * *